(12) United States Patent
Shankar et al.

(10) Patent No.: US 6,442,428 B1
(45) Date of Patent: Aug. 27, 2002

(54) IMPLANTABLE CARDIAC STIMULATION DEVICE HAVING A PROGRAMMABLE RECONFIGURABLE SEQUENCER

(75) Inventors: Balakrishnan Shankar; Kenneth R. McNeil, II, both of Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/805,671

(22) Filed: Mar. 13, 2001

(51) Int. Cl.$^7$ ................................................ A61N 1/36
(52) U.S. Cl. .......................................................... 607/9
(58) Field of Search .................................. 607/9, 5, 30

(56) References Cited

U.S. PATENT DOCUMENTS

| | | | |
|---|---|---|---|
| 5,464,435 A | 11/1995 | Neumann | 607/9 |
| 5,466,254 A | 11/1995 | Helland | 607/123 |

*Primary Examiner*—Scott M. Getzow

(57) ABSTRACT

A pacemaker or implantable cardioverter defibrillator is provided with a microcontroller having a general purpose microprocessor for performing high-level device functions and a sequencer for performing routine pacing functions. The general purpose microprocessor is programmed using an instruction set capable of general programming applications. The sequencer is programmed using a very simple instruction set having instructions selected only for performing routine pacing functions. The sequencer may be, for example, a programmable state machine. By providing a programmable sequencer for controlling routine pacing operations, the microprocessor is thereby free to devote its resources to performing high-level functions. Hence, the microprocessor may be operated at a lower clock frequency than would otherwise be needed if the microprocessor were also required to perform routine pacing functions and power savings are thereby achieved. By controlling all routine pacing operations using the programmable sequencer, the routine operations are thereby more expediently and reliably performed. Also, because software for the sequencer is developed using only the simple instruction set associated therewith, pacing software is quickly and reliably developed. Additional benefits are gained by isolating the pacing software from the high-level functional software to permit, for example, the microprocessor software to be replaced without affecting the sequencer software, and vice versa. Also, a method is described for generating an integrated circuit having a configuration optimized based upon predetermined software requirements. The method may be used to design the sequencer.

11 Claims, 11 Drawing Sheets

IMPLANTABLE CARDIAC STIMULATION DEVICE HAVING A PROGRAMMABLE RECONFIGURABLE SEQUENCER

FIELD OF THE INVENTION

The invention generally relates to implantable cardiac stimulation devices and in particular to a hardware and software architecture for use therein.

BACKGROUND OF THE INVENTION

A wide range of implantable cardiac stimulation devices are provided for surgical implantation into humans. One common example is the cardiac pacemaker. Another is the implantable cardioverter defibrillator (ICD). Current state of the art implantable devices typically include a general purpose programmable microprocessor for controlling the functions of the device such as detecting medical conditions within the patient in which the device is implanted and administering appropriate therapy. Within a pacemaker, for example, the microprocessor monitors the detection of P-waves and R-waves to determine whether an episode of bradycardia has occurred and, if so, administers a pacing pulse to the heart. Within an ICD, for example, the microprocessor analyzes P-waves, R-waves and other electrical signals of the heart to determine if an episode of ventricular fibrillation has occurred and, if so, administers a defibrillation shock to the heart.

In addition to performing functions directed to administering immediate therapy, the microprocessor coordinates all other functions of the implantable device such as: monitoring the power source of the device to determine if the power source needs to be replaced; switching of the mode of operation of the device from, for example, a single-chambered pacing mode to a dual-chambered pacing mode; and recording events for diagnostic purposes such as P-waves and R-waves, mode switching events and the administration of therapy. As implantable cardiac stimulation devices become more and more sophisticated, the number and complexity of functions that must be performed by the microprocessor increases as well. As a result, it becomes more and more difficult for the microprocessor to perform routine pacing functions while also performing the many higher level functions. To ensure that routine pacing functions are performed in a timely manner, faster and more powerful microprocessors are employed, resulting in greater power consumption in the device.

Accordingly, it would be desirable to provide an improved hardware architecture for use within an implantable cardiac stimulation device which eliminates the need for the microprocessor to perform routine pacing functions, thereby permitting the microprocessor to devote its resources primarily to performing higher level functions and it is to that end that aspects of the present invention are directed.

Also, when using a powerful general purpose microprocessor within an implantable cardiac stimulation device, it becomes increasingly difficult to develop software for controlling the microprocessor in a reliable and expedient manner. In this regard, a powerful microprocessor typically operates using a large and complex instruction set. Accordingly, software developed for controlling the microprocessor may need to be equally complex, resulting in a greater amount of time devoted to developing the software and still further time required for debugging the software. Also, with a microprocessor exploiting a complex instruction set, the risk of software bugs or other errors arising in the software becomes more significant. Accordingly, it would also be desirable to provide an improved software architecture for use within an implantable cardiac stimulation device, which expedites the prompt development of reliable software for use with implantable devices and it is to that end that other aspects of the invention are directed.

Insofar as both hardware and software development for implantable cardiac stimulation devices is concerned, it would be desirable to provide an improved technique for developing both the hardware and the software so as to ensure that the hardware and the software are optimized for use with one another to perform the required functions of the device, such as pacing functions, defibrillation functions, etc. In particular, it is desirable to provide an improved technique for developing hardware and software that minimizes development costs and also minimizes power consumption within the resulting device. Other aspects of the invention are directed to these ends.

SUMMARY OF THE INVENTION

In accordance with one aspect of the invention, an implantable cardiac stimulation device is provided for delivering therapy to heart tissue. The stimulation device includes a sensing circuit for sensing a cardiac signal from the heart tissue and an electrical therapy delivery circuit for delivering therapy to the heart tissue. A controller is provided which includes a programmable sequencer for analyzing the cardiac signal to determine whether therapy is needed and for controlling the electrical therapy delivery circuit to deliver therapy. The controller also includes a separate general purpose programmable microprocessor for performing non-therapy-delivering operations.

In an exemplary embodiment, wherein the implantable cardiac stimulation device is a pacemaker, the programmable sequencer controls routine pacing operations such as detection of P-waves and R-waves and the delivery of anti-bradycardia pacing pulses in response thereto. The programmable sequencer employs only a limited instruction set having twenty-two non-arithmetic instructions optimized for controlling routine pacing operations. In contrast, the programmable microprocessor is a complex instruction set computing (CISC) microprocessor or a conventional reduced instruction set computing (RISC) using a full instruction set. The programmable microprocessor is programmed to control all other operations of the pacemaker, such as lead impedance monitoring, battery monitoring and the storage of internal electrocardiogram (IEGM) signals and pacing events for subsequent transmission to an external programming device for analysis.

By providing a programmable sequencer for controlling routine pacing operations or other "low-level" functions, the microprocessor is thereby free to devote its resources to performing all other "high-level" functions. Hence, the microprocessor may be operated at a lower clock frequency or duty cycle than would otherwise be needed if the microprocessor were also required to perform routine pacing functions, thereby saving power. By controlling all routine pacing operations with a programmable sequencer or state machine, the pacing operations are thereby more expediently performed. Moreover, because software for the sequencer is developed using only the first instruction set, routine pacing software is more expediently developed. Other higher level functions of the microprocessor are programmed using a more complex instruction set for performing a wider range of functions. Additional benefits are gained by isolating routine pacing software from the higher level functional software to permit, for example, the software of the microprocessor to be replaced without affecting the software of the sequencer, or vice versa. Both the microprocessor and sequencer may be reprogrammed after the device has been implanted within a patient by transmitting updated software into the device from an external programmer device.

In one specific example, the sequencer is an event-driven programmable state machine programmed to transition through a sequence of states based upon a sequence of instructions selected from the first instruction set. In another specific example, the sequencer is implemented as a RAM-based state machine.

In accordance with another of the invention, a system and method is provided for developing a sequencer for use in an implantable cardiac stimulation device. In accordance with the method, a high-level software program is developed setting forth the functions to be performed by the sequencer using a high-level software design language. The high-level software program is then compiled to determine a minimum set of instructions needed to implement the functions. An automated hardware optimization tool processes the instructions to determine an optimal high-level hardware design for implementing the instructions. The high-level hardware configuration is output in a high-level hardware design language. The high-level hardware design is then processed using an automated hardware design tool to determine an optimal gate configuration. Thereafter, an integrated circuit (IC) sequencer is fabricated incorporating the optimal gate configuration.

In this manner, an IC is developed having the optimal transistor configuration to perform the operations required by the previously developed software. Thus, in contrast with many conventional techniques which merely optimize an IC configuration based upon a high-level hardware design, the method of the invention first optimizes the high-level hardware design based upon the software design, then optimizes the IC design based upon the optimized hardware design. Depending upon the particular implementation, the IC design may be optimized to, for example, minimize the number of transistor devices, circuit space, power consumption, or signal transmission routing delays. In this manner, once software has been designed to perform desired functions, a hardware device having the optimal IC configuration is easily developed based upon the software.

Additional advantages and features of the various aspects of the invention will be apparent from the descriptions below in combination with the accompanying drawings. Method and apparatus embodiments of the various aspects of the invention are provided.

BRIEF DESCRIPTION OF THE DRAWINGS

Further features and advantages of the invention may be more readily understood by reference to the following description taken in conjunction with the accompanying drawings, in which:

FIG. 17 illustrates an event buffer for use with the sequencer of FIG. 10.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
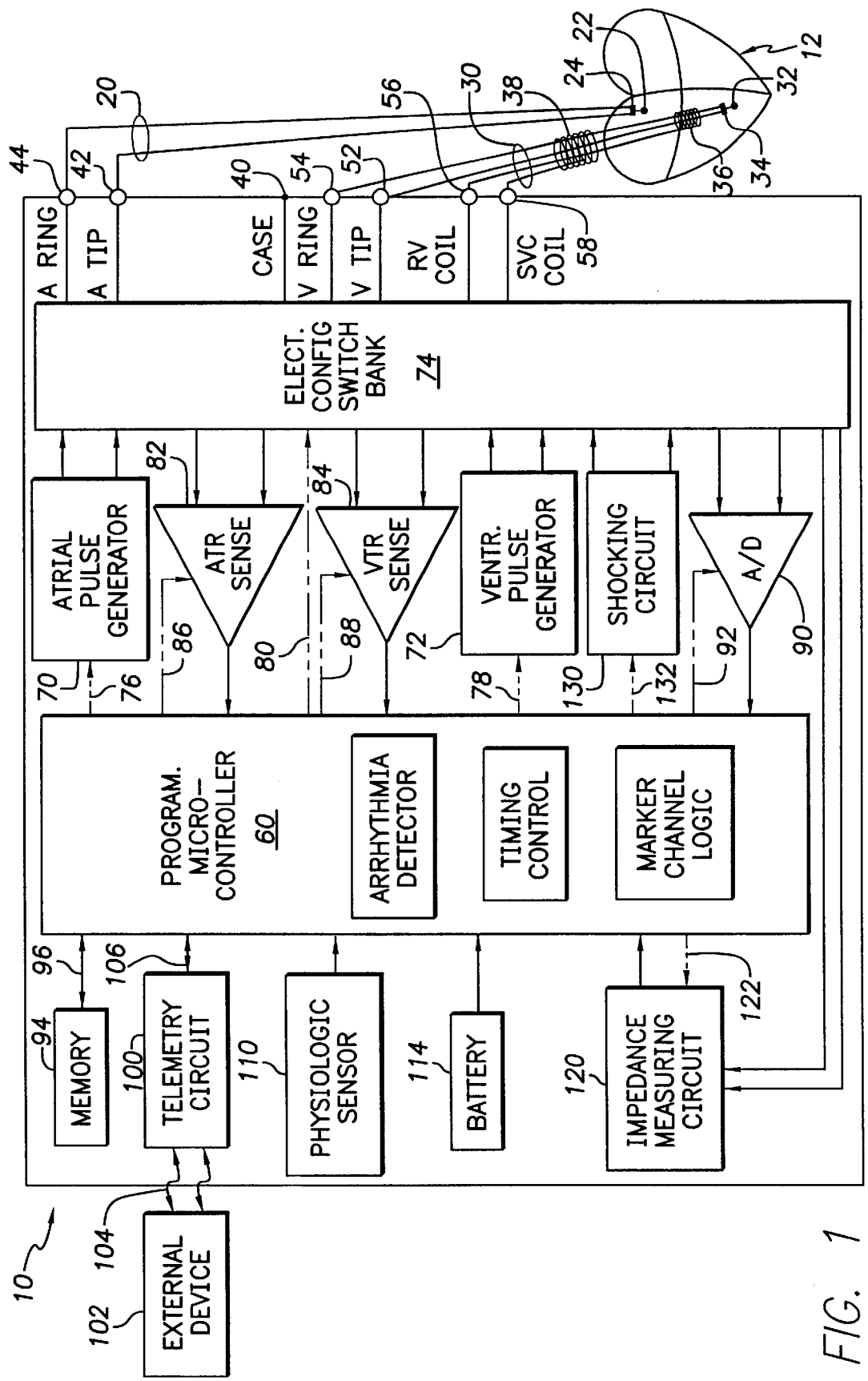
FIG. 1 is a functional block diagram of a dual-chamber implantable cardiac stimulation device illustrating the basic elements of a stimulation device which can provide cardioversion, defibrillation and pacing stimulation.

In FIG. 1, a simplified block diagram is shown of a dual-chamber implantable stimulation device 10 which is capable of treating both fast and slow arrhythmias with stimulation therapy, including cardioversion, defibrillation, and pacing stimulation. While a dual-chamber device is shown, this is for illustration purposes only, and one of skill in the art could readily eliminate or disable the appropriate circuitry to provide a single-chamber stimulation device capable of treating one chamber with cardioversion, defibrillation and pacing stimulation.

To provide atrial chamber pacing stimulation and sensing, the stimulation device 10 is shown in electrical communication with a patient's heart 12 by way of an implantable atrial lead 20 having an atrial tip electrode 22 and an atrial ring electrode 24 which typically is implanted in the patient's atrial appendage.

The stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an superior vena cava (SVC) coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals, and delivering stimulation in the form of pacing and shock therapy to the right ventricle.

While only two leads are shown in FIG. 1, it is to be understood that additional stimulation leads (with one or more pacing, sensing and/or shocking electrodes) may be used in order to efficiently and effectively provide pacing stimulation to the left side of the heart or atrial cardioversion and/or defibrillation. For example, a lead designed for placement in the coronary sinus region could be implanted to deliver left atrial pacing, atrial shocking therapy, and/or for left ventricular pacing stimulation. For a complete description of a coronary sinus lead, see U.S. patent application Ser. No. 09/196,898, "A Self-Anchoring Coronary Sinus Lead" (Pianca et al.), and U.S. Pat. No. 5,466,254, "Coronary Sinus Lead with Atrial Sensing Capability" (Helland), which patents are hereby incorporated herein by reference.

The housing 40 (shown schematically) for the stimulation device 10 includes a connector (not shown) having an atrial pin terminal 42 and an atrial ring terminal 44, which are adapted for connection to the atrial tip electrode 22 and the atrial ring electrode 24, respectively. The housing 40 further includes a ventricular pin terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode, or anode, alone or in combination with one of the coil electrodes, 36 and 38. For convenience, the names of the electrodes are shown next to the terminals.

At the core of the stimulation device 10 is a programmable microcontroller 60 which controls the various modes of stimulation therapy. Various embodiments of the microcontroller 60 are described in detail below. The microcontroller 60 includes the ability to process or monitor input signals (data) as controlled by a program code stored in a designated block of memory.

As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the operation of the stimulation device timing of such stimulation pulses. The microcontroller also includes an autocapture threshold detection system described in greater detail below.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art. An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the device 10 to deal effectively with the difficult problem of sensing the low frequency, low amplitude signal characteristics of ventricular fibrillation. The outputs of the atrial and ventricular sense amplifiers, 82 and 84, are connected to the microcontroller 60 which, in turn, inhibit the atrial and ventricular pulse generators, 70 and 72, respectively, in a demand fashion whenever cardiac activity is sensed in the respective chambers.

For arrhythmia detection, the invention utilizes the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through the established communication link 104.

In the preferred embodiment, the stimulation device 10 further includes a physiologic sensor 110. Such sensors are commonly called "rate-responsive" sensors. The physiological sensor 1 10 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the invention and is shown only for completeness. The stimulation device additionally includes a battery 114 which provides operating power to all of the circuits shown in FIG. 1. For the stimulation device 10, which employs shocking therapy, the battery must be capable of operating at low current drains for long periods of time, and then be capable of providing high-current pulses (for capacitor charging) when the patient requires a shock pulse (preferably, in excess of 2 A, at voltages above 2 V, for periods of 10 seconds or more). The battery 114 must also have a predictable discharge characteristic so that elective replacement time can be detected. Accordingly, the invention employs lithium/silver vanadium oxide batteries, as is true for most (if not all) such devices to date. As further shown in FIG. 1, the invention preferably includes an impedance measuring circuit 120 for measuring the impedance of the leads which is enabled by the microcontroller 60 by a control signal 122. The impedance measuring circuit 120 is not critical to the invention and is shown for only completeness.

Depending upon the implementation, the device may function as an implantable cardioverter/defibrillator (ICD) device. That is, it detects the occurrence of an arrhythmia, and automatically applies an appropriate electrical shock therapy to the heart aimed at terminating the detected arrhythmia. To this end, the microcontroller 60 further controls a shocking circuit 130 by way of a control signal 132. The shocking circuit 130 generates shocking pulses of low (up to 0.5 Joules), moderate (0.5–10 Joules), or high energy (11 to 40 Joules), as controlled by the microcontroller 60. Such shocking pulses are applied to the patient's heart through at least two shocking electrodes, and as shown in this embodiment, using the RV and SVC coil electrodes, 36 and 38, respectively. In alternative embodiments, the housing 40 may act as an active electrode in combination with the RV electrode 36 alone, or as part of a split electrical vector using the SVC coil electrode 38 (i.e., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 2:
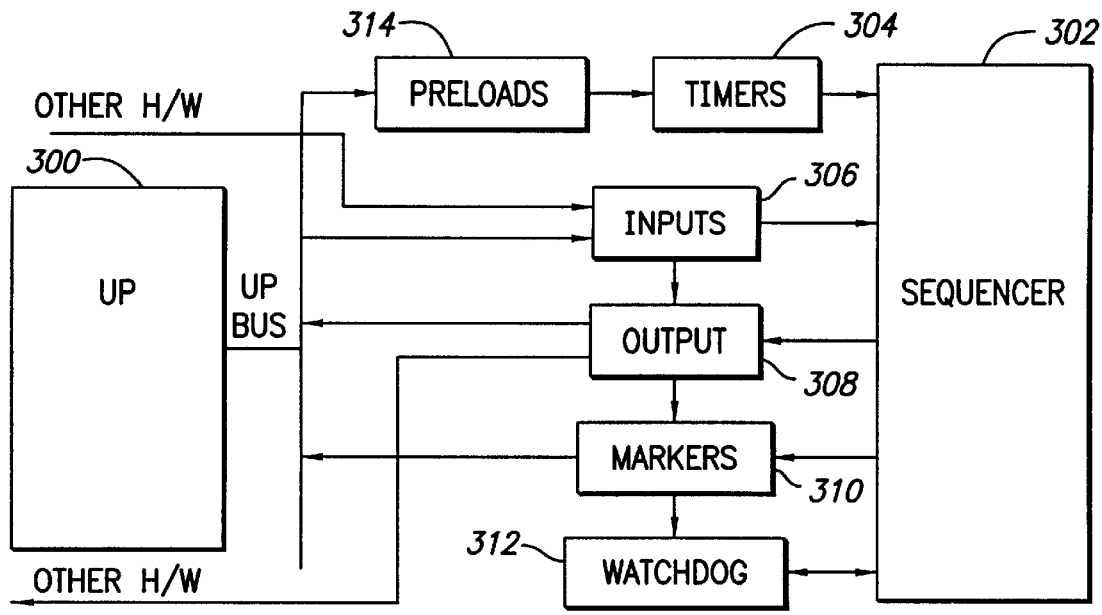
FIG. 2 is a block diagram of a first exemplary embodiment of the microcontroller of the implantable cardiac stimulation device of FIG. 1, particularly illustrating a general purpose microprocessor and separate programmable sequencer for use therein.

FIG. 2 illustrates a first exemplary implementation of controller 60 of FIG. 1 having a microprocessor 300 for performing high-level functions and a sequencer 302 for performing routine pacing functions or other low-level functions. The microprocessor is programmed, using a complex instruction set or a conventional reduced instruction set, to perform the high-level functions of the pacemaker, such as recording diagnostic information, periodically checking the power supply, coordinating receipt and transmission of signals to or from an external programmer device and the like. The sequencer, in contrast, performs routine pacing functions, such as bradycardia pacing, mode switching, and the like, based upon a very simple instruction set having instructions tailored to performing those operations. By providing a sequencer for performing routine pacing operations, the microprocessor is thereby free to perform the higher level functions without also needing to perform the pacing functions. Hence, the microprocessor may be run at a significantly slower clock rate than might otherwise be required thereby saving power. An exemplary instruction set for the sequencer is provided in Table I.

TABLE I

| Instruction Name | Description |
| --- | --- |
| CFGT | Configure Timer (2, 4, 8 ms, or as counter) |
| CLKT | Clock Timer (in counter configuration) |
| CLRF | Clear Input Falling Edge Latch |
| CLRO | Clear Output (output = 0) |
| CLRR | Clear Input Rising Edge Latch |
| JUMP | Jump to address |
| LOAD | Load Timer with Immediate Value |
| MARK | Load Marker Latch with Immediate Value |
| MASK | Mask all RESUME signals |
| PRLD | Load Timer with Preload Register |
| PULO | Pulse Output |
| SETO | Set Output (output = 1) |
| TSTF | Test Input Falling Edge Latch, Branch if set |
| TSTI | Test Input Status, Branch if set |
| TSTO | Test Output Status, Branch if set |
| TSTR | Test Input Rising Edge Latch, Branch if set |
| TSTT | Test Timer Status, Branch if Timer = 0 |
| UNMF | Unmask Input Falling Edge Latch RESUME |
| UNMR | Unmask Input Rising Edge Latch RESUME |
| UNMT | Unmask Timer Timeout RESUME |
| WAIT | Enter SLEEP mode and wait for RESUME |
| WDOG | Service (preload) Watchdog Timer |

Briefly, the various instructions operate to control or to access timer circuits, input circuits, output circuits and the like. To this end, the microcontroller of FIG. 2 includes a set of timers 304 for timing selected operations on behalf of the sequencer, an input block 306 for providing input signals to the sequencer either from the microprocessor or from other hardware components such as sense amplifiers 82 and 84 of FIG. 1, and an output block 308 for receiving output commands from the sequencer for routing to either the microprocessor or other hardware components such as pulse generators 70 and 72 of FIG. 1. A preload circuit 314 is provided for loading initial timer values into the timers under the control of the microprocessor. For example, the microprocessor may program the various timers with initial values for timing absolute refractory periods, relative refractory periods, cardiac cycles and the like. The microcontroller also includes an event marker block 310 for receiving diagnostic event markers generated by the sequencer for routing to the microprocessor and to an external programmer device. Also, a watch dog circuit 312 is provided for resetting the sequencer in the event a predetermined time period has elapsed without appropriate behavior by the sequencer. The watch dog circuit operates as a fail safe circuit to ensure reliable operation of the overall device. The various components of FIG. 2 will now be described in greater detail with reference to FIGS. 3–7.

Figure 3:
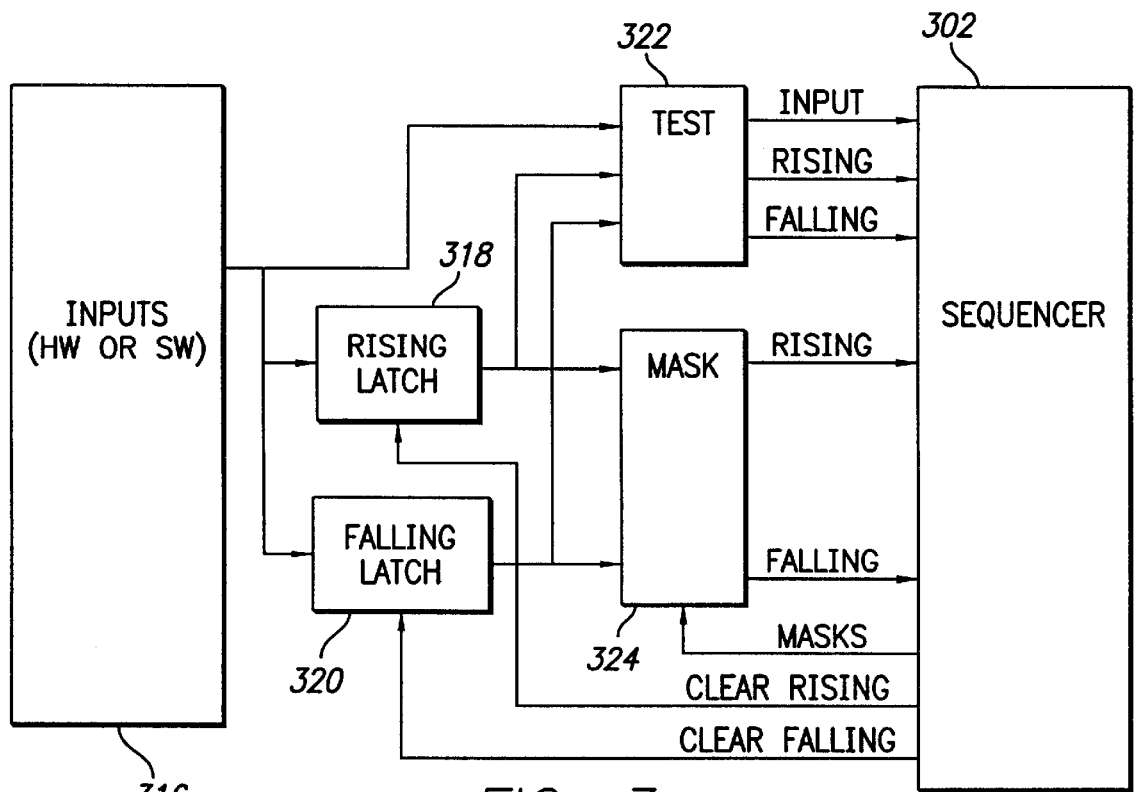
FIG. 3 illustrates an input block portion of the microcontroller of FIG. 2.

Input block 306 is illustrated in FIG. 3 and includes an input unit 316 for receiving input signals from either the microprocessor or other hardware components of the device such as the sense amplifiers. The inputs are routed to both a rising latch 318 and a falling latch 320. Rising latch 318 latches the input values at each rising edge of a clock signal of the microcontroller provided on a clock line (not separately shown). Falling latch 320 latches input signals at each falling edge of the clock signal. Since the input values may change during a clock signal, the values in the rising latch and falling latch may differ.

Signals provided by the rising and falling latches are routed through a test circuit 322 and a mask circuit 324. The test circuit also receives the input values directly from input block 316. The test signal is used by the sequencer to determine if a particular event or input has occurred or is currently active (i.e. to test rising edge latch, falling edge latch, or current state of input—high or low). Mask circuit 324 filters the input signals received from the rising and falling latches in accordance with binary masks received from the sequencer. For example, if the input pattern generated by input block 316 is a 16-bit pattern, the mask circuit may mask out all but the first three bits of the input pattern. By providing a mask circuit responsive to masks generated by the sequencer, the sequencer thereby efficiently controls the number of input signals received at any particular time, based upon its internal programming. In addition to generating masks for controlling the operation of mask circuit 324, the sequencer also outputs signals to clear values latched within the rising and falling latches, also based upon the internal programming of the sequencer. Within the Table I, the input falling latch is cleared using a CLRF instruction and the input rising edge latch is cleared using a CLRR instruction. A MASK instruction operates to mask the signals output from the rising and falling latches. The UNMF and UNMR instructions operate to unmask selected portions of the input signals received either via the falling latch or the rising latch. Although not shown in Table I, both the UNMF and UNMR instructions receive operands specifying the particular bits of the input signal pattern to be unmasked.

Figure 4:
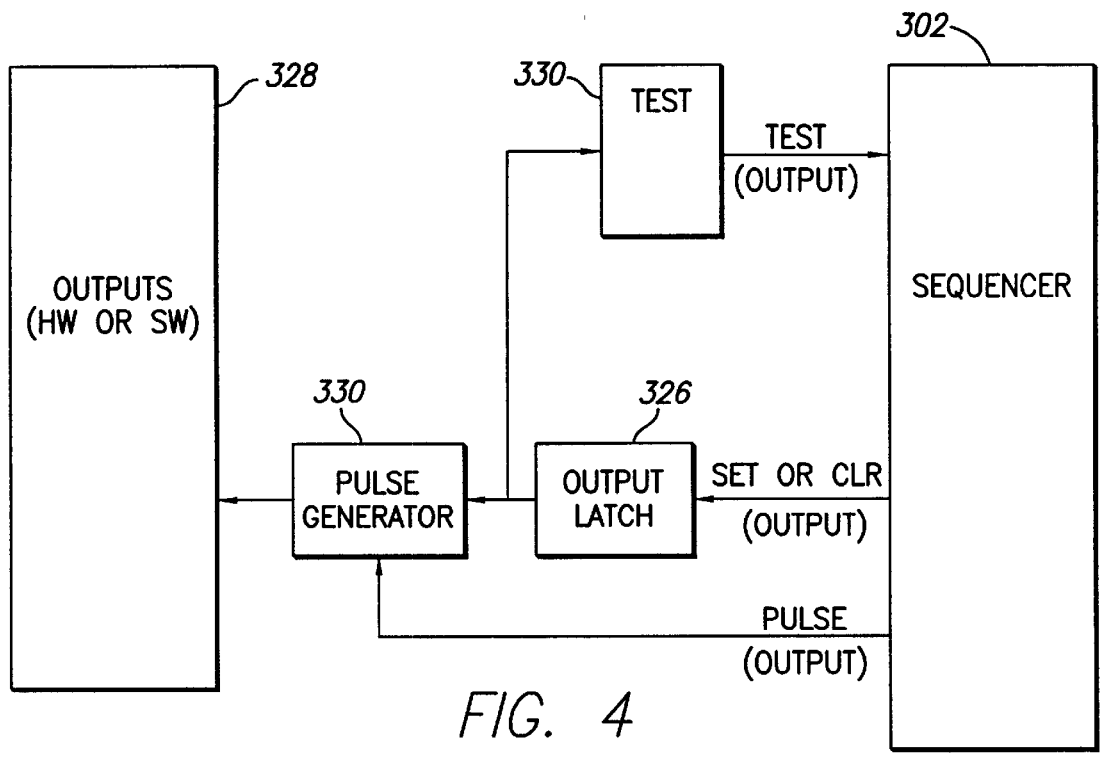
FIG. 4 illustrates an output block portion of the microcontroller of FIG. 2.

FIG. 4 illustrates components of output block 308. Briefly, output signals are applied to an output latch 326, which latches the signals once each clock cycle. To forward the output signals to external hardware and software components (328), the sequencer asserts a pulse signal to a pulse generator 330 which routes the values currently latched in the output latch to the output block 328. The output values are also routed through a test block 330 for feedback into the sequencer. The test signal is used by the sequencer to determine the state of a particular output (high or low).

The output block of FIG. 4 is controlled by the following instructions. The PULO instruction operates to transmit the pulse output signal to pulse generator 330. The SETO instruction sets selected values within the output latch to a high logic value of one. Selected bits of the output latch are cleared using the CLRO instruction. Both the SETO and CLRO instructions receive operands specifically identifying the bits of the output pattern to be set. The overall output pattern may be, for example, 16 bits. Also, the TSTO instruction tests the output status by examining the test circuit output signal provided by test circuit 330. The TSTO command is a branch command which, if the test pattern indicates that the test result is true, causes the sequencer to branch to an alternative sequence of instructions preprogrammed within the sequencer.

Figure 5:
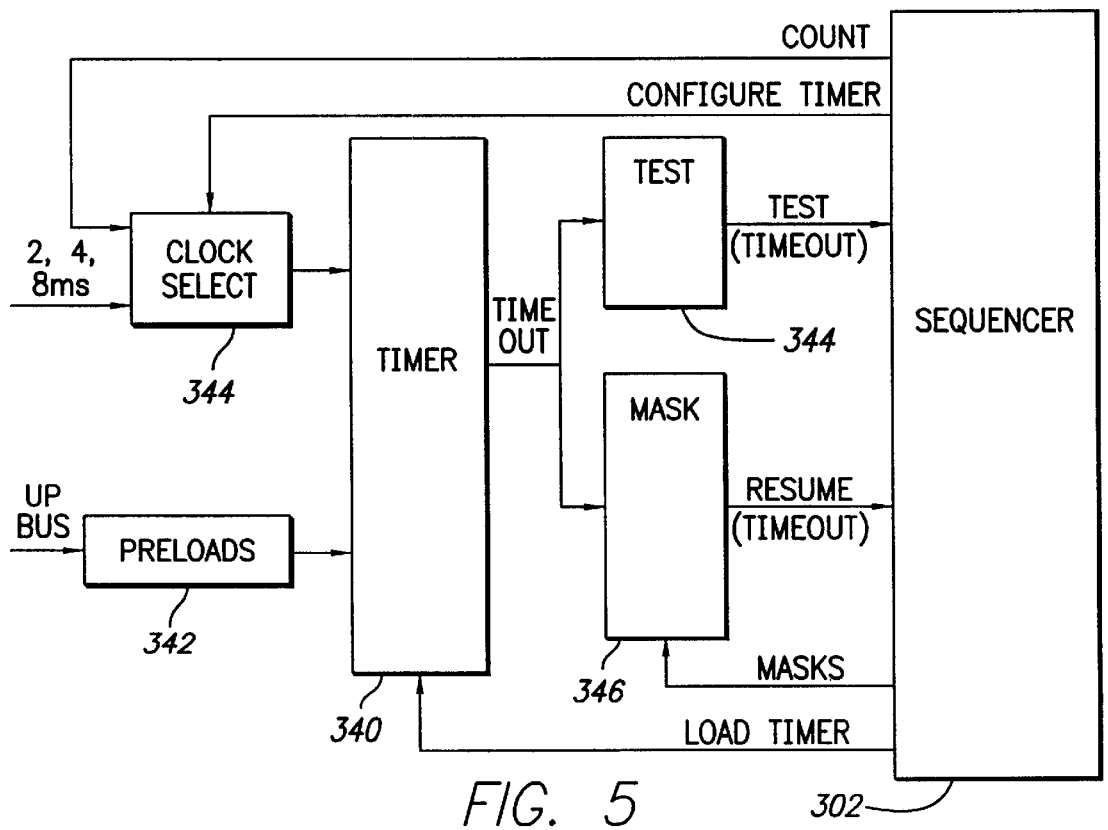
FIG. 5 illustrates a timer block portion of the microcontroller of FIG. 2.

FIG. 5 illustrates components of the timer block of FIG. 2. Briefly, a set of timers 340 are preloaded with timer values received from the microprocessor via a preload circuit 342. The timers also receive clock signals received from a clock select circuit 344 which, as shown, may select among a variety of clock signals of differing frequencies. The timer circuit also receives specific timer values from the sequencer, after the sequencer begins operating. Hence, the values provided by the preload circuit are merely default values for use by the sequencer when it begins operation or when it resumes following a reset operation. In any case, based upon the current values of the timers, and upon the selected clock signal, timer block 340 times various periods on behalf of the sequencer, such as absolute refractory periods, relative refractory periods and the like. When one of the timers within timer block 340 times out, a time out signal is sent both to a test block 344 and a masking circuit 346. The test circuit is used by the sequencer to determine if a particular timer has timed out. Mask circuit 346 masks the overall bit pattern of the timer output signal, based upon masks received by the sequencer and outputs a RESUME signal to the sequencer. For example, if the timer block includes sixteen timers, but the sequencer has only activated a first timer, then the sequencer transmits a mask to the mask circuit to mask out all output values from the timers other than the output bit associated with the first timer.

The sequencer controls and accesses the components of the timer block using the following instructions set forth in Table I. A CFGT instruction operates to configure the timer by controlling the clock select block to select one of the input clock signals. Alternatively, the CFGT instruction controls the clock select unit to operate as a counter. Appropriate operands are provided within the CFGT instruction. A CLKT instruction is provided to activate timer block 340 if configured as a counter. A UNMT instruction operates to unmask bits previously masked using masking circuit 346. A MASK instruction operates to mask all RESUME signals. Finally, a PRLD instruction operates to load a particular timer with a timer value via preload register 342.

Figure 6:
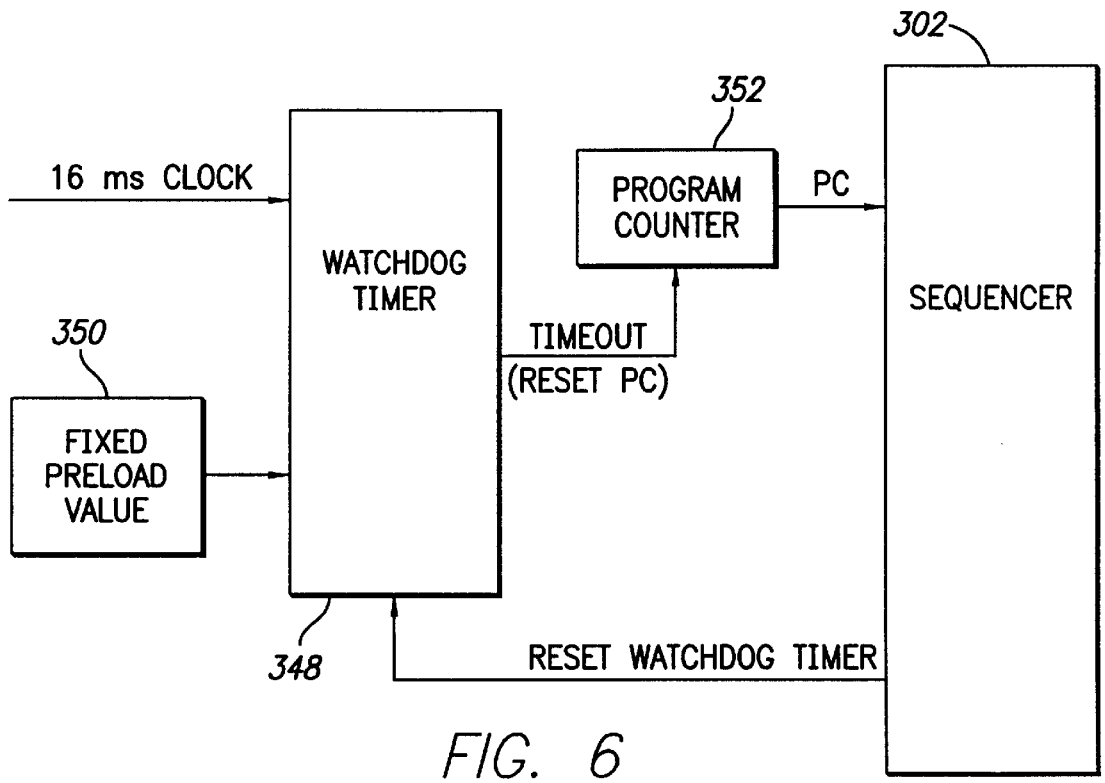
FIG. 6 illustrates a watch dog block portion of the microcontroller of FIG. 2.

FIG. 6 illustrates components of the watch dog block of FIG. 2. Briefly, watch dog timer circuit 348 continuously times a watch dog time period based upon a fixed preloaded value provided by fixed block 350 using a sixteen millisecond clock signal. The time period may be, for example, two seconds. If the sequencer operates correctly, a reset signal will be transmitted from the sequencer to the watch dog timer before the watch dog timer times out. Hence, so long as the sequencer is operating correctly, the watch dog timer will never time out. If the sequencer fails to operate reliably, the watch dog timer will ultimately time out causing a time out signal to be routed via program counter 352 to the sequencer, in turn causing the sequencer to reset to a first instruction. In this manner, the sequencer is reset in the event anomalous behavior occurs, which may arise, for example, if electromagnetic interference from a device external to the pacemaker causes electrical signal values manipulated by the sequencer to switch to an inappropriate state. The watch dog timer is controlled by the WDOG instruction which causes the watch dog timer to reset to the preloaded value provided by fixed preload circuit 350.

Figure 7:
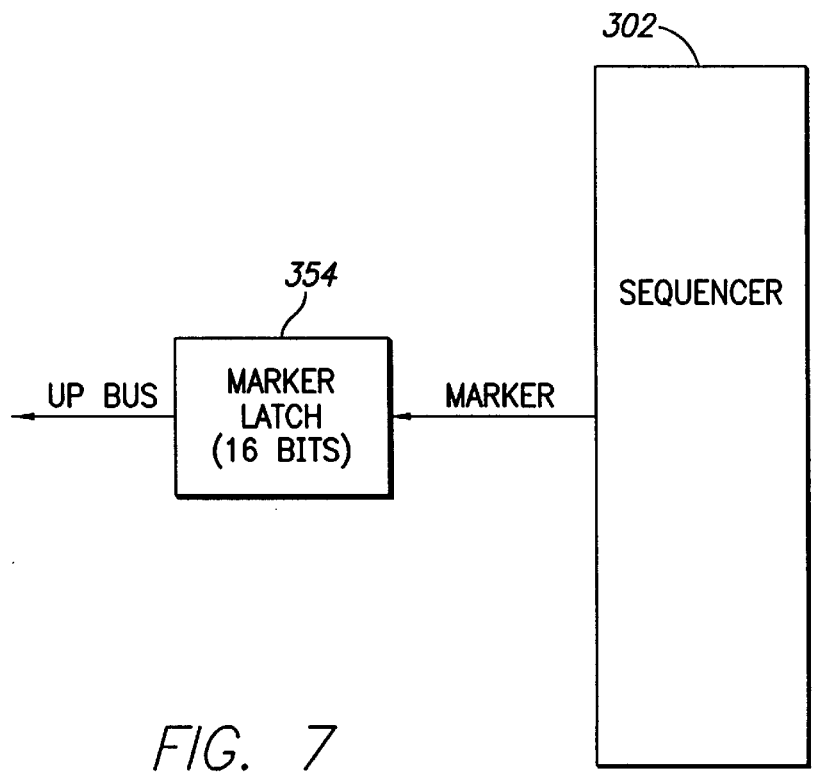
FIG. 7 illustrates a marker block portion of the microcontroller of FIG. 2.

FIG. 7 further illustrates the event marker block of FIG. 2. Briefly, event markers generated by the sequencer are routed to an event marker latch 354, which is sixteen bits wide. The event marker latch latches the values once per clock cycle and routes the currently latched values to the microprocessor for further manipulation. Values stored within the sixteen bits of the event marker latch may be, for example, bits representative of events detected by the sequencer, such as P-waves, R-waves, mode switching events, error events, and the like. The event marker block is controlled using an MARK instruction.

Additional instructions are provided to control operations within the sequencer. Specifically, a JUMP instruction is provided to cause the sequencer to internally jump to a new sequence of commands, as specified by an internal address or other pointer. Also, a WAIT instruction controls the sequencer to enter a sleep mode to wait for a resume command to be generated by the timer block. Hence, when the wait instruction is performed, the sequencer suspends processing of any further instructions until a RESUME command is received. As one example, the sequencer may remain in the sleep state during an absolute refractory period until a timer tracking the absolute refractory period has timed out.

Based upon the simple set of instructions set forth in Table I, the sequencer performs routine pacing operations such as VVI mode pacing, VDD mode pacing and the like. Table II provides source code for controlling the sequencer to perform VVI mode pacing. An assembled version of the source code, specifying a particular sequence of instructions performed by the sequencer is set forth in Table III.

TABLE II

| | | |
|---|---|---|
| DEFINE_TIMERS (Trate, Tvref); | | 'define timers |
| DEFINE_INPUTS (Erwave); | | 'define inputs |
| DEFINE_OUTPUTS (Vpulse); | | 'define outputs |
| DEFINE_MARKERS (Mrwave, Mvpulse) | | 'define markers |
| VREF: | START (Trate, Tvref); | 'start timers |
| | WATCHDOG; | 'service watchdog |
| | WAIT (Tvref); | 'wait for Tvref to timeout |
| | CLEAR (Erwave); | 'ignore any Erwave events during Vref |
| VAD: | WAIT (Trate, Erwave); | 'wait for Trate to timeout or Erwave event |
| | If Erwave GOTO RWAVE | 'if Erwave detected then branch to RWAVE |
| | | 'otherwise Trate timed out so output pulse |
| VPULSE: | OUTPUT (Vpulse); | 'deliver Vpulse |
| | MARKER (Mvpulse); | 'send Vpulse marker |
| | GOTO VREF; | 'start next cardiac cycle |
| RWAVE: | MARKER (Mrwave) | 'send Rwave marker |
| | GOTO VREF; | 'start next cardiac cycle |

TABLE III

| | | |
|---|---|---|
| VREF: | PRLD Trate, Prate | 'Load Trate timer with Prate preload register |
| | PRLD Tvref, Pvref; | 'Load Tvref timer with Pvref preload register |
| | WDOG; | 'Service watchdog |
| | MASK; | 'Mask all RESUME signals |
| | UNMT Tvref; | 'Unmask Tvref RESUME signal |
| | WAIT; | 'Wait for RESUME |
| | CLRR Erwave; | 'Clear Erwave rising edge latch |
| VAD: | MASK; | 'Mask all RESUME signals |
| | UNMT Trate; | 'Unmask Trate RESUME signals |
| | UNMR Erwave; | 'Unmask Erwave rising edge RESUME signal |
| | WAIT; | 'Wait for RESUME |
| | TSTR Erwave, RWAVE; | 'Test Erwave rising edge signal |
| VPULSE: | PULO Vpulse; | 'Output Vpulse |
| | MARK Mvpulse; | 'Send Vpulse marker |
| | JUMP VREF; | 'Jump to VREF to start next cardiac cycle |
| RWAVE: | MARK Mrwave; | 'Send Rwave marker |
| | JUMP VREF; | 'Jump to VREF to start next cardiac cycle |

Figure 8:
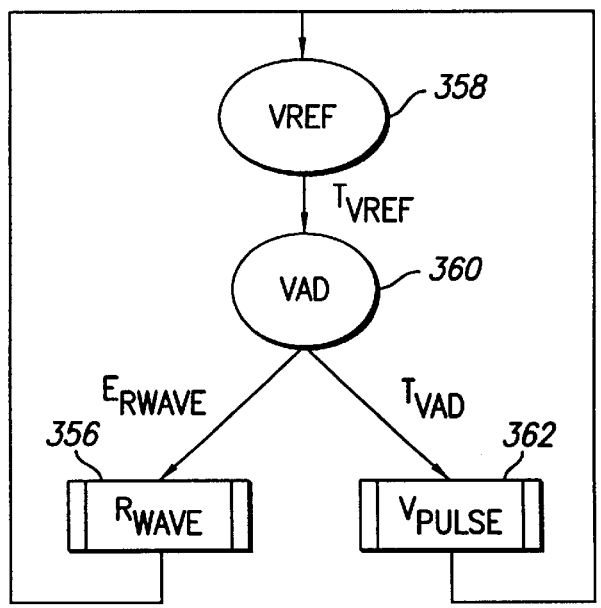
FIG. 8 illustrates a method for performing VVI mode pacing using the microcontroller of FIG. 2.
Figure 9:
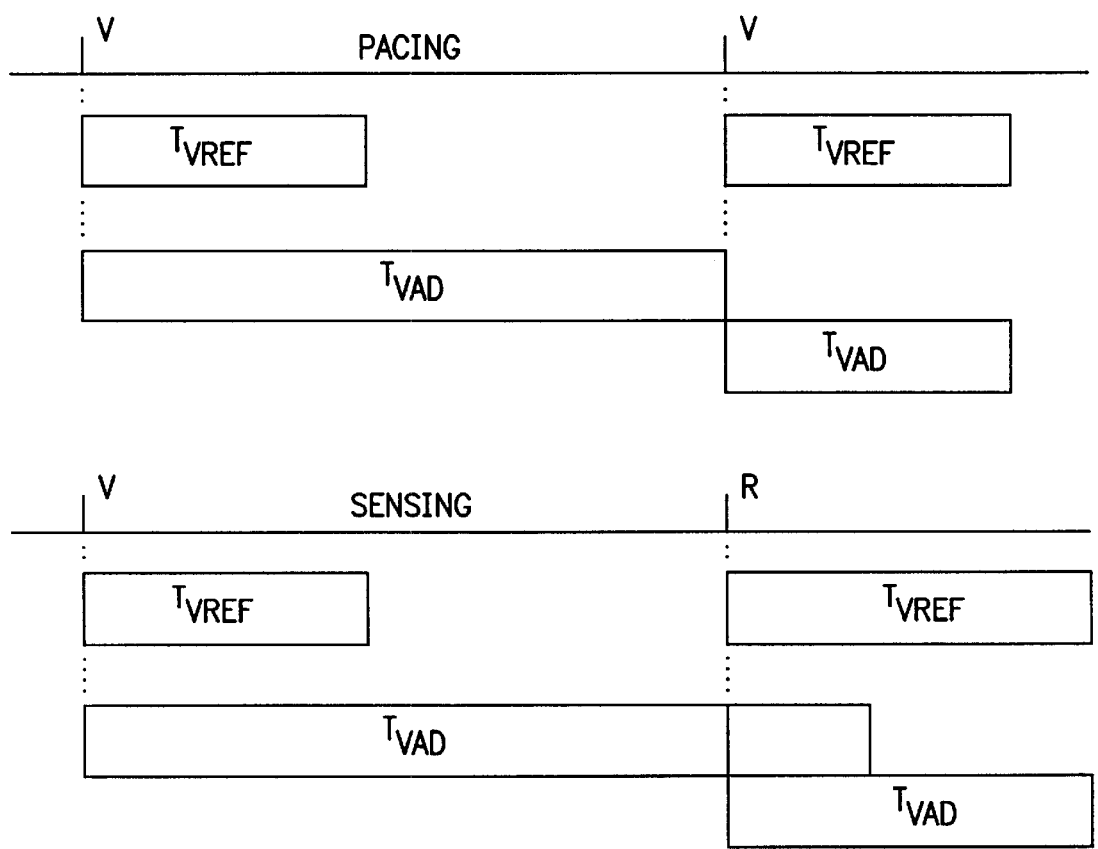
FIG. 9 illustrates pacing and sensing states processed by the microcontroller of FIG. 2 while performing the VVI mode pacing operation of FIG. 8.

FIG. 8 is a flow chart illustrating the method performed by the sequencer when programmed with the assembly code of Table III to perform VVI pacing operations. FIG. 9 is a timing diagram illustrating the duration of the various states of FIG. 8 as timed under the control of the sequencer.

Briefly, referring first to FIG. 8, after an R-wave is detected in state 356 the sequencer transitions to a VREF state 358 wherein the sequencer times a ventricular refractory period. The steps performed by the sequencer during the VREF state are set forth in Tables II and III. The duration of the ventricular refractory period is also illustrated in FIG. 9. Once the refractory period has been timed, the sequencer transitions to a VAD state 360 wherein a ventricular atrial delay period is timed. If another R-wave is detected before the completion of the VAD period, then execution returns to the R-wave state. Otherwise, the sequencer switches to a V pulse state 362 and generates a V pulse. In either case, the sequencer returns to the VREF state for timing the resulting refractory period. The case where the VAD period times out before an R-wave is detected is shown within a top portion of FIG. 9. The case wherein an R-wave is detected before the VAD period elapses is shown within a bottom portion of FIG. 9.

Figure 10:
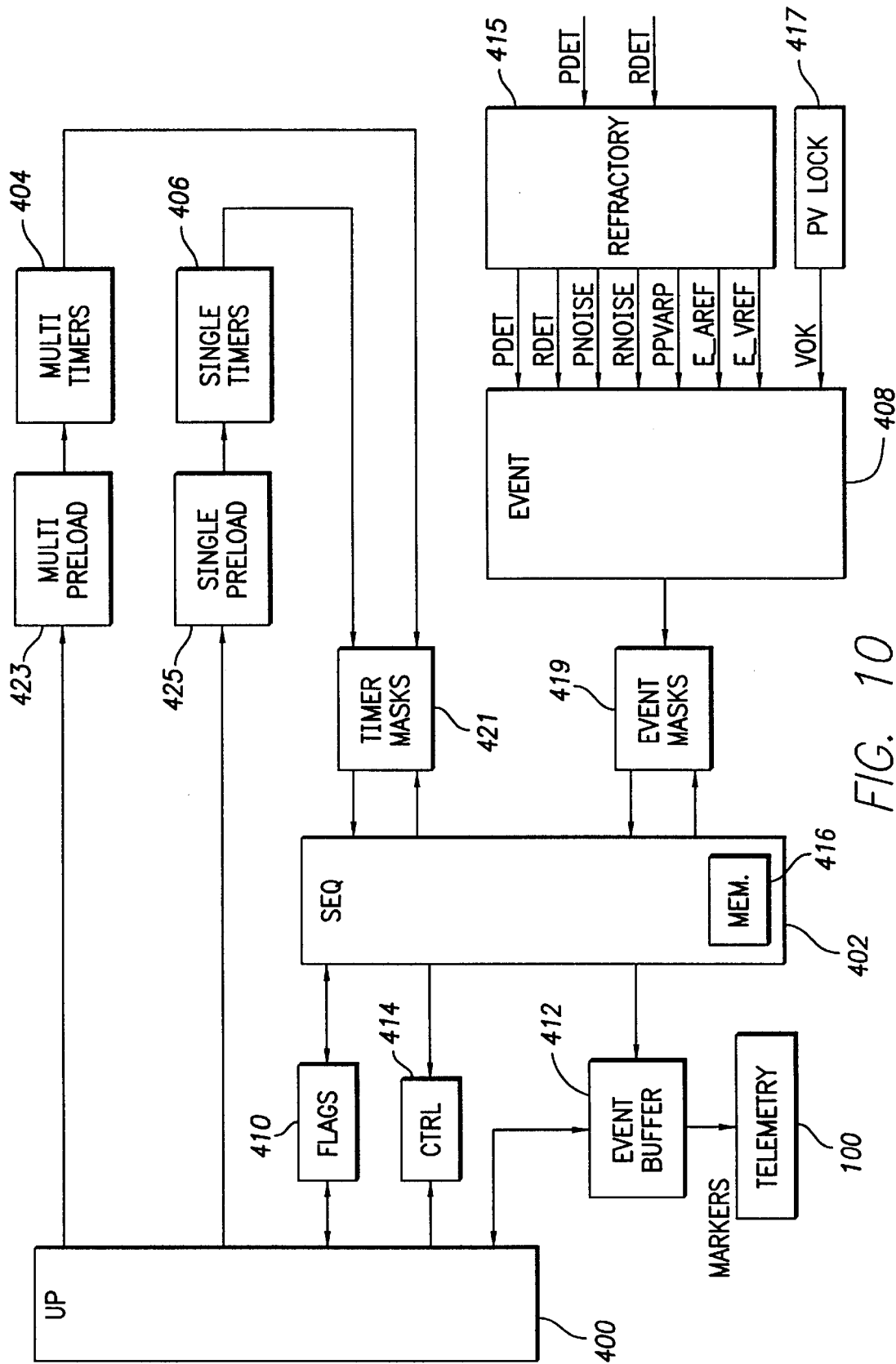
FIG. 10 is a block diagram of a second exemplary embodiment of the microcontroller of the implantable cardiac stimulation device of FIG. 1.

FIG. 10 illustrates pertinent components of a second exemplary embodiment of microcontroller 60 of FIG. 1. The microcontroller includes a general programmable microprocessor 400 and a programmable sequencer 402.

Table IV below provides another exemplary instruction set for use by sequencer 402. As can be seen, the instructions are primarily directed to manipulating various hardware devices, such as timers, latches, flag bits, and the like, provided in connection with the microprocessor and sequencer. Other instructions are directed to perform branching operations, such as jump operations, sub-routine call operations and the like.

TABLE IV

Instruction Set

| Section | # Bytes | Neumonic | Instruction | Operand(s) |
|---|---|---|---|---|
| Timers | 1 | PREM, T#, R# | Load Multi-Timer | Timer Number & Pre-load Register |
| | 1 | PRES, T# | Load Single-Timer | Timer Number |
| | 2 | PREM2 | Load Multi-Timers & Single-Timers | Timer Numbers & Pre-load Registers |
| | 2 | TSTT, T# | Test Multi-Timer or Single-Timer | Timer Number & Branch Address |
| Events | 2 | CLRE, E# | Clear Events | Event Numbers |
| | 2 | TSTE, E# | Test Event | Event Number & Branch Address |
| Flags | 1 | SETF, F# | Set Flag | Flag Number |
| | 1 | CLRF, F# | Clear Flag | Flag Number |
| | 2 | TSTF, F# | Test Flag | Flag Number & Branch Address |
| Event Buffer | 1 | STEC | Write Event Code to Buffer | Event Code |
| Control | 2 | STCR | Pulse Controls | Control Numbers |
| Branching | 2 | JMP | Jump | Branch Address |
| | 2 | SUB | Call Subroutine | Subroutine Address |
| | 1 | RET | Return from Subroutine | |
| Wait | 2 | WAIT1 | Wait for Timers &/or Special Events | Timer Numbers &/or Event Numbers |
| | 3 | WAIT2 | Wait for Timers &/or any Events | |

More specifically, the instructions performed by the sequencer manipulate or respond to values stored within a set of multi-load timers 404, a set of single load timers 406, a set of event latches 408, a set of flag bits 410, and an event buffer 412. Additionally, the sequencer may output signals to a control circuit 414 which permits the sequencer to control other components of the device, shown in FIG. 1, such as pulse generators and the like.

Briefly, the multi-load timers are directed to timing states that do not last the duration of a cardiac cycle and are mutually exclusive to one another. Examples are the AV delay and the VA delay. The single load timers, in contrast, are used to time states or parameters that may last the entire duration of a cardiac cycle, such as a maximum tracking interval. Signals output from the multi-load timers and the single-load timers are filtered using a timer mask block 421 before input into sequencer 402. The masks employed within mask block 421 are generated by the sequencer. The multi-load timers and the single-load timers include pre-load circuit blocks 423 and 425, respectively, to be described in greater detail below.

The event latches permit detection of intrinsic cardiac events, such as the detection of P-waves or R-waves, and/or other events, such as the end of a refractory period, to redirect the path of the sequencer. For example, detection of a P-wave will cause values in the event latches to be reset, possibly triggering a jump command by the software of the sequencer. The events stored in the event latches are pre-processed by a refractory circuit 415 which initially receives signals identifying the detection of a P-wave or R-wave (PDET or RDET). Refractory circuit 415 analyzes PDET and RDET to determine, for example, whether the signals are actually representative of P-waves or R-waves, or instead are representative of noise, or perhaps representative of a post-ventricular atrial refractory period (PVARP). These or other output signals are transmitted from the refractory circuit into the event latch block 408. Event latch block also receives a VOK signal from a PV block 417 circuit which indicates whether a V pulse is permitted. Briefly, after a V pulse, no additional V pulses are allowed during a time period measured by the VOK timer. Once the timer has timed out, the VIK signal is asserted to indicate that another V pulse is then permitted. Thus, the VOK signal limits the ventricular pacing rate. Any events latched in event block 408 are filtered by masks stored in event mask block 419 under the control of sequencer 402. The flag bits permit the sequencer to save information for evaluating later in a sequence of commands. The flag bits also enable the microprocessor to control the sequencer based upon higher level algorithms performed by the microprocessor. The control bits enable the sequencer to control operation of other hardware components, such as pulse generators, etc. Finally, the event buffer is used by the sequencer to record and time stamp a history of significant events for output as markers via the telemetry circuit 100 of FIG. 1. The events within the event buffer may be accessed and manipulated by the microprocessor and may also be transmitted to a telemetry unit for transmission to the external programmer. The functions of the various hardware components will be described in greater detail below with reference to the remaining figures.

In addition to controlling the sequencer by storing appropriate bits within the flag bit registers 410, the microprocessor may reprogram the sequencer itself by downloading a new set of instructions therein. The instructions may be initially received via telemetry unit 100 from the external programmer. In this manner, software upgrades to the sequencer are easily performed without requiring removal of the implanted device.

Programming the sequencer may be performed as follows. Software programs for performing routine pacing operations are written using a high-level sequencer programming language, an example of which is provided in Appendix A attached hereto. The example of Appendix A provides for DDD pacing. A compiler converts the high-level software language to sequences of instructions based upon the instructions set of Table IV. The instructions are encoded in binary form then downloaded, via the microprocessor or directly, into a memory 416 of the sequencer.

Figure 11:
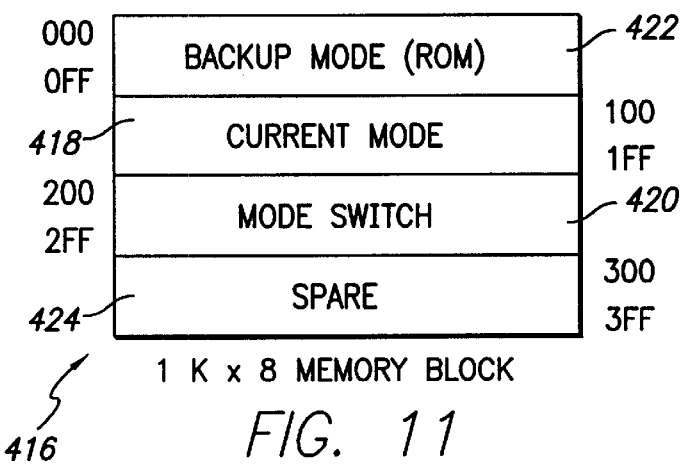
FIG. 11 illustrates a memory configuration for use with the sequencer of FIG. 10.

An exemplary memory configuration for memory 416 of the sequencer is shown in FIG. 11. As can be seen, the memory includes a first programmable portion 418 for performing a current mode of operation. A second portion of memory includes sequences of binary commands for performing an alternative mode of operation. As one example, memory portion 418 may include sequences of commands for performing dual chambered pacing. Memory portion 420 may include sequences of commands for performing singled chambered pacing, for use subsequent to a mode switch. A third portion of the memory 422 provides commands for a backup mode of operation. Memory portion 422 is read only memory (ROM), to ensure that it cannot be accidentally corrupted or overwritten. Hence, if a malfunction is detected in the programs stored within the current mode or mode switch portions of memory, the sequencer reverts to the backup mode stored within memory portion 422 which provides a standard set of routine pacing commands. Finally, a fourth portion of memory 424 is spare memory, which may be used to store data or the like, or may be provided to accommodate larger software programs that may be subsequently downloaded from the external programmer to replace previous sequencer programs.

Figure 12:
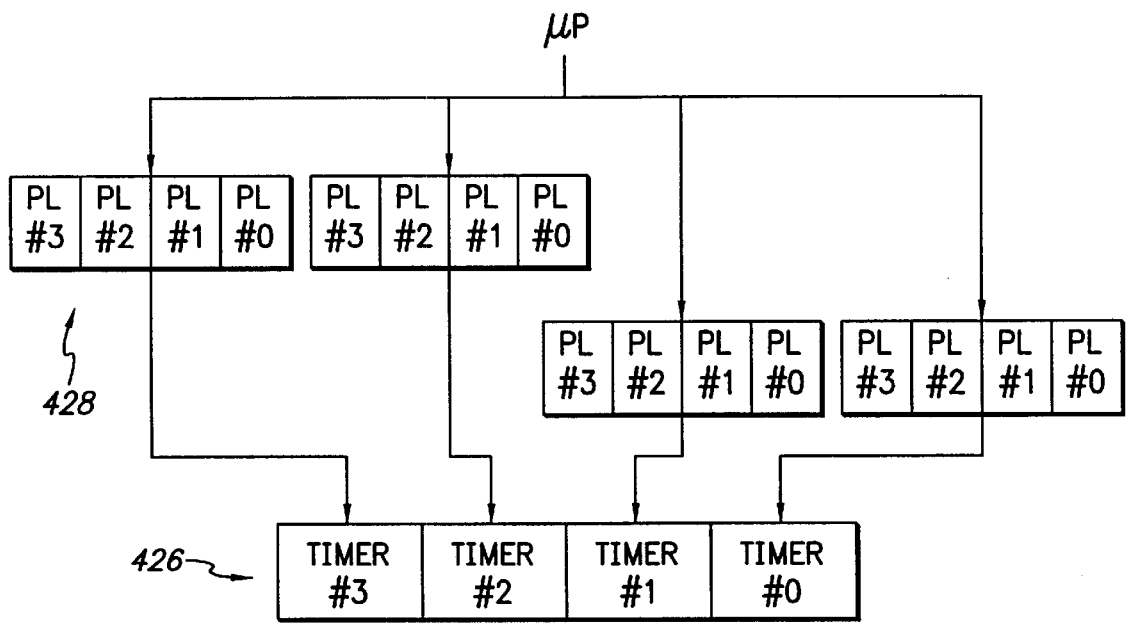
FIG. 12 illustrates a set of multi-load timers for use with the sequencer of FIG. 10.

As noted, a set of multi-load timers are provided for timing intervals that do not last the duration of a cycle and which are mutually exclusive. FIG. 12 illustrates the multi-load timers, and sets of preload timers used in conjunction therewith. Briefly, a set of four multi-load timers 426 are provided, each having a set of four preload timers 428 associated therewith. In use, the microprocessor writes values into the preload registers to control the timing of the corresponding multi-load timer. Hence, each individual timer can be preloaded with one of four timing intervals. In general, the timing intervals depend upon the particular state that is to be timed. Exemplary states are the aforementioned AVD and VAD states.

To use the timers of FIG. 12, the sequencer of FIG. 10 sends control signals to activate the timers after the timers have been preloaded with the appropriate timing intervals. Thereafter, based upon the programming of the sequencer, the sequencer may wait for one of more of the timers to time out, then perform various operations. Alternatively, the sequencer waits until one timer has elapsed, then checks to determine whether one of the other timers has also elapsed and, if not, performs a branching operation using the aforementioned jump instruction. In still other cases, the sequencer evaluates one or more of the multi-load timers upon completion of a timing operation performed by one of the single-load timers.

Figure 13:
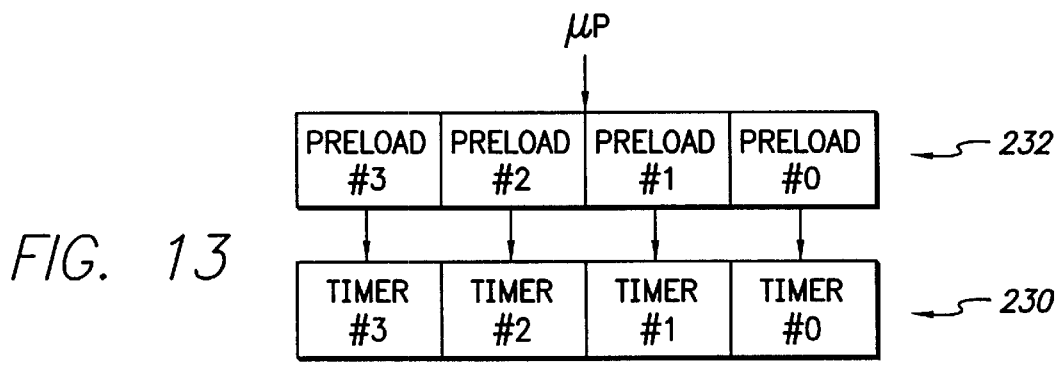
FIG. 13 illustrates a set of single-load timers for use with the sequencer of FIG. 10.

The single load timers are illustrated in FIG. 13. Briefly, a set of four single load timers 430 are provided, each capable of timing an interval that may last the entire duration of a cardiac cycle. Each single load timer has a single preload register 432 associated therewith. Hence, each single load timer can be preloaded with only a single interval, as specified by the microprocessor. An example of a state which may be timed using a single load timer is the maximum tracking interval.

In use, the sequencer activates one or more of the timers, then depending upon the programming of the sequencer, waits until selected timers elapse, then performs additional instructions. Alternatively, once one timer has elapsed, the sequencer evaluates another timer to determine whether it has also elapsed and, if not, the sequencer jumps to a new set of instructions. In still other examples, the values timed by the multi-load timers are evaluated first, before determining whether to branch based upon timing operations of the single load timers. As can be appreciated, a wide range of timing operations may be performed by using the multi-load and single load timers, with various intervals programmed therein by the microprocessor.

Figure 14:
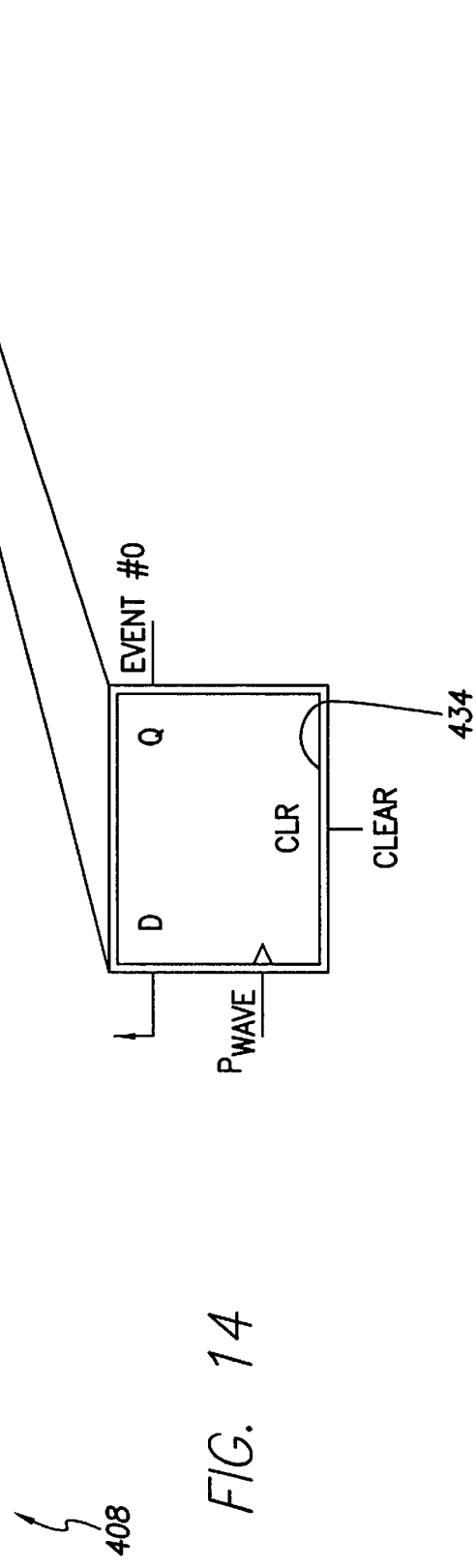
FIG. 14 illustrates a set of event latches for use with the sequencer of FIG. 10.

The sequencer also responds to the values stored within event latches 408 of FIG. 10. An exemplary set of event latches is illustrated in FIG. 14. Briefly, twelve event latches are provided, each of which may be configured as a D latch 434. The latches serve to store intrinsic events, such as the detection of P-waves or R-waves, or hardware events, such as the detection of the end of a refractory period. To this end, each latch has an input hard-wired to one of the other devices of the implantable cardiac stimulation device, such as to one of the sense amplifiers or the like.

In use, in one example, the sequencer is programmed to wait until an event is registered within one of the event latches. In other cases, the sequencer is programmed to periodically evaluate a particular event latch, and branch to a new sequence of operations if an event is latched therein. Periodically, the sequencer clears one or more of the events within the event latches. By providing a set of twelve event latches, a wide variety of events may be captured therein, permitting the sequencer to perform a wide variety of pacing operations based upon the presence or absence of recorded events.

Figure 15:
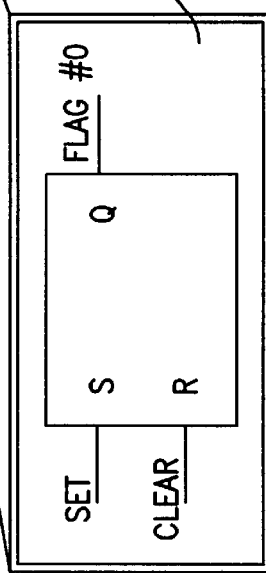
FIG. 15 illustrates a set of flag bits for use with the sequencer of FIG. 10.

Flag bits 410 of FIG. 10 are illustrated in FIG. 15. Each flag bit may be implemented using an SR latch 436, as shown. Eight flag bits are provided, each accessible by either the sequencer or the microprocessor for the purposes of recording data for subsequent processing. The sequencer may set or clear the various flag bits as required by its internal programming. Alternatively, the sequencer may test a particular flag bit and branches to a new set of instructions if the flag bit is set.

Figure 16:
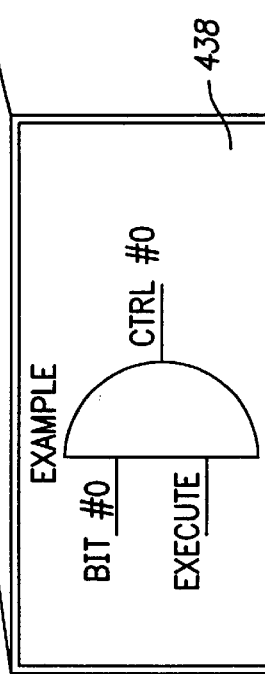
FIG. 16 illustrates a set of control bits for use with the sequencer of FIG. 10.

Control register 414 of FIG. 10 is shown in more detail in FIG. 16. Briefly, twelve control bits are provided, each of which may be configured as an AND gate 438, as shown. The flag bits are provided for permitting the sequencer to control other hardware resources within the device, such as pulse generators and the like. In use, the sequencer, based upon its internal programming, may pulse one or more of the control bits. The sequencer asserts a logic value of one or zero on a bit input line of the control bit, then asserts an execute signal to permit the control bit to be passed to a control bit output, which is connected to a particular hardware resource.

Event buffer 412 of FIG. 10 is shown in more detail in FIG. 17. Briefly, the event buffer is capable of storing thirty-two events codes, along with a corresponding time stamp. Individual events codes indicate, for example, a mode switching event, or the detection of a P-wave or R-wave. Both the sequencer and microprocessor can write event codes into the buffer. The microprocessor can also read from the buffer to, for example, determine the result of a sequence of operations performed by the sequencer during a previous cardiac cycle.

A pair of pointers are provided for use with the event buffer. A sequencer pointer identifies the event most recently inserted into the buffer by the sequencer. A marker pointer indicates the event most recently accessed by the microprocessor. The sequencer pointer permits the event buffer to be employed as a circular buffer, to ensure that each new event overwrites the oldest of the previous events. The marker pointer permits the microprocessor to track events independently from the sequence in which they are entered into the buffer.

Figure 18:
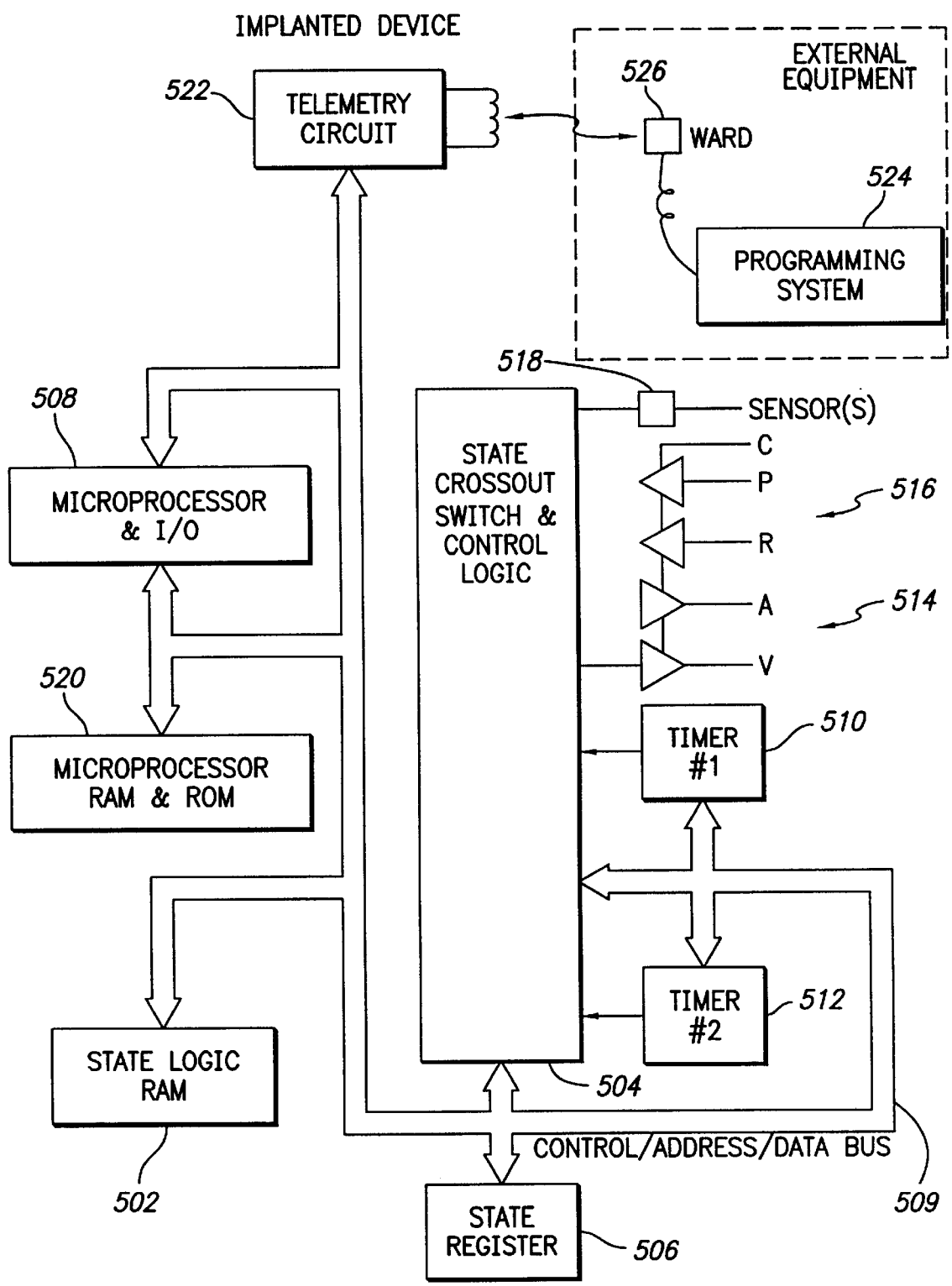
FIG. 18 is a block diagram of a third exemplary embodiment of the microcontroller of the implantable cardiac stimulation device of FIG. 1, particularly illustrating a RAM-based state machine for use with a microprocessor.

FIG. 18 illustrates an embodiment of the microcontroller of FIG. 1 wherein the sequencer is implemented as a RAM-based state machine. The RAM-based state machine performs a sequence of operations similar to that performed by the sequencers of the preceding embodiments. Briefly, the state machine of FIG. 18 includes state logic RAM 502, state crosspoint switch & control logic 504 and state register 506. These devices operate in conjunction with a microprocessor 508 and a pair of first and second timers 510 and 512 (or a third timer if needed) interconnected via a bus 509. The state machine also operates in conjunction with various other devices of the implantable cardiac stimulation device external to the microcontroller which, for ease of describing the operation of the state machine, are also illustrated within FIG. 18. In particular, the state machine operates in conjunction with a pair of pulse generators 514, a pair of sense amplifiers 516, one or more sensors 518, microprocessor RAM and ROM memory 520 and a telemetry circuit 522. Also shown in FIG. 18 is an external programming system 524 which communicates with the telemetry circuit 522 using a wand 526 manually positionable over the chest of the patient in the vicinity of the implanted stimulation device.

The state logic RAM selects the system inputs and outputs and timer outputs that determine the next state of the state register. The state crosspoint switch & control logic creates the logical connection of the system inputs and outputs and timer outputs to the state register. The contents of the state logic RAM can be modified by input from the programming system either before or after the device is implanted in the patient. An important feature of the state machine is that the various states programmed therein and the logic controlling the transition from one state to another are not fixed but can be reprogrammed simply by downloading new values for storage within the state logic RAM from the external programming system.

Now describing the operation of the state machine in greater detail, the state register stores a state number specifying the current state of the system. Within each state, the implanted device performs certain predetermined functions, such as waiting for detection of a P-wave or asserting a pacing pulse. Once the operations specified for the particular state have been completed, the state machine transitions to another state having another state number. The state to be transitioned to depends upon the various values received from the timers, sense amplifiers and sensors as well as inputs received from the microprocessor or from RAM and ROM. More specifically, the number in the state register changes when an interval of time expires, a group of one or more events occurs, or a combination of a group of one or more events occurs within or after an interval of time. For example, atrial pulse generation, which may be represented as state # 23, will transition to an AV delay state, which may be represented as state # 17, when an atrial pulse interval expires. In another example, an atrial escape alert interval state, which may be represented as state # 5, transitions to an AV delay state, which may be represented by state # 17, when a valid P-wave is detected. As noted above, for each state, the state logic RAM specifies the particular system inputs and outputs and the timer outputs to be used in determining the next state. The state crosspoint switch & control logic includes a set of AND/OR gates which specify the logical connection of the system inputs and outputs and the timer outputs to thereby yield a new value for storage within state register 506 based upon the current values of the various timers and input signals. The configuration of AND/OR gates of the state crosspoint switch & control logic is predetermined so as to provide a wide variety of possible state register output values based upon the various input values. The values of the state logic RAM, in contrast, can be reprogrammed to change the input values to be processed by the control logic for each state to thereby allow reprogramming of the overall operations of the state machine. The design and programming of state machines to perform specific functions is well known in the art and will not be described in further detail herein.

Insofar as state logic RAM 502 is concerned, it may be provided with information specifying multiple modes of operation, for permitting the state machine to easily transition from one mode of operation to another. Additionally, a default mode of operation may be stored within a state logic ROM (not separately shown) so that, in the event the implantable cardiac stimulation device malfunctions, the device can automatically switch to a default mode of operation stored within the ROM.

Thus, various embodiments of a microcontroller for an implantable cardiac stimulation device have been described wherein high-level functions are performed by a generally programmable microprocessor and routine pacing functions are performed by a sequencer. The various embodiments share many advantages. By eliminating the need for the microprocessor to perform routine pacing functions, the overall clock speed and/or duty cycle of the microprocessor can be significantly reduced, thereby saving power and increasing device longevity, while still permitting the microprocessor to perform its high-level functions in a timely manner. Meanwhile, the sequencer performs the routine functions at a high clock rate sufficient to perform the pacing functions in a timely manner. Since the sequencer performs relatively few operations, the sequencer can be implemented using relatively small hardware devices consuming relative little power. Preferably, the software code used by the sequencer or used by the state logic RAM in the case of the RAM-based state machine, is merely downloaded one time, as with the software of the microprocessor. The external programmer need not interact directly with the sequencer. Rather, all interactions with the sequencer are handled by the microprocessor, as with any other hardware block of the implantable cardiac stimulation device. Considerable flexibility is achieved, in part, because no restrictions are imposed by the sequencer architecture for pulse sequences or event-to-event transitions, as may occur with other hardware devices for directly controlling pacing operations. Moreover, the sequencer code can be designed to perform any state transition and the various system resources, such as inputs, outputs, timers, preload registers, etc., are implemented in a general unrestricted manner (i.e., any preload register can be loaded for use with any timer). As one example of the flexibility of the sequencer, the operation of the sequencer can be reprogrammed to sense and pace in an additional chamber of the heart merely by adding code to pulse additional hardware outputs with the correct sequence and timing. Also, much of the flexibility of the sequencer is achieved because the sequencer employs an event driven architecture, rather than an interrupt driven architecture as typically used with a generally programmable microprocessor. Hence, interrupt signals need not be processed and prioritized and the sequencer need not suspend current operations to respond to an interrupt as is typically required with a microprocessor.

Another significant advantage of the sequencer is that maintainability of the overall implantable device is enhanced. In particular, the pacing code of the sequencer is isolated from the software of the microprocessor to permit either portion of software to be replaced or upgraded without necessarily affecting the software of the other device. Debugging is facilitated, particularly in the embodiment employing event marker capability, by merely storing all state sequences and transitions using the event markers. Logic analyzer support may be provided by multiplexing sequencer signals to external chip I/O pads and providing custom coding of the instruction set into the logic analyzer, which is easily implemented particularly given the very few instructions required by the sequencer. Also, on chip integrated circuit emulation (ICE) capability can be provided including single step emulation modes, break points, and trace buffers. Programming of the sequencer is very easy, given the very limited instruction set required by the sequencer. Moreover, with the provision of appropriate compilers and the like, the software for the sequencer may be written initially in a high-level language. Custom tools and integrated development environment (IDE) protocols may be implemented to handle all steps of the development process, as with other types of software. The isolation of the sequencer software from microprocessor software permits greater reuse of the sequencer software. For example, the sequencer software may be used in a number of different devices having different microprocessors, although differences between microprocessors may require some changes to the sequencer software depending upon the particular configuration. Safety and reliability of the implanted device is also enhanced, in part, by isolating the critical pacing therapy functions performed by the sequencer from the higher level operations performed by the microprocessor. Thus, for example, should the software of the microprocessor fail, perhaps as a result of an undetected software bug, the patient still receives pacing therapy under the control of the sequencer. Also, latency problems which may occur with a microprocessor required to respond to a wide variety of interrupts are avoided. As noted, the sequencer is not interrupt driven, but merely event-driven, ensuring a minimum of latency problems. The sequencer may be tested using conventional automated test pattern generation (ATPG) tools scalable to handle different configurations of sequencers, such as sequencers performing only pacing operations or sequencers additionally performing telemetry operations. Sequencer testing is easily performed using standard input bits to replace hard-wired inputs such as P-wave and R-wave detection inputs. Software in the microprocessor can be written to perform all of the necessary test protocols for testing the sequencer.

Thus, the various embodiments of the sequencer described herein have many advantages, not the least of which is a significant reduction in power consumption of the overall device achieved by permitting the microprocessor to operate at a much lower clock rate or duty cycle while the sequencer performs necessary pacing operations. To further minimize power consumption of the sequencer, the method of FIG. 19 may be employed which permits a sequencer IC to be developed having the minimal number of transistors necessary to perform the required functions of the device. Briefly, the method is performed as follows. At step 600, system engineers define system requirements, i.e., the system engineers determine the specific functions to be performed by the sequencer. The requirements may be represented in software using a high-level software design language. At step 602, the high-level software program is compiled using a compiler, which extracts the minimum set of instructions necessary for performing the functions of the software thus fulfilling all of the requirements of the software. To this end, the compiler is preprogrammed with a global set of possible instructions which may be performed by a sequencer. By analyzing the high-level software program, the compiler identifies the sub-set of instructions necessary to perform the actual operations required by the software. The sub-set of instructions is then processed at step 604 by an automated hardware optimization tool to generate a high-level hardware design configuration in a high-level design language such as Verilog. At step 606, the high-level hardware design language is processed using an automated hardware design tool, such as a logic synthesizer, to determine the optimal arrangement of transistors for implementing the hardware design generated at step 604. In other words, the logic sequencer outputs a specific set of logic gates for implementing the sub-set of instructions. An IC is then manufactured at step 608 using the transistor configuration generated by the logic synthesizer, thereby yielding an IC optimized to perform the specific functions specified by the high-level software design program.

Figure 19:
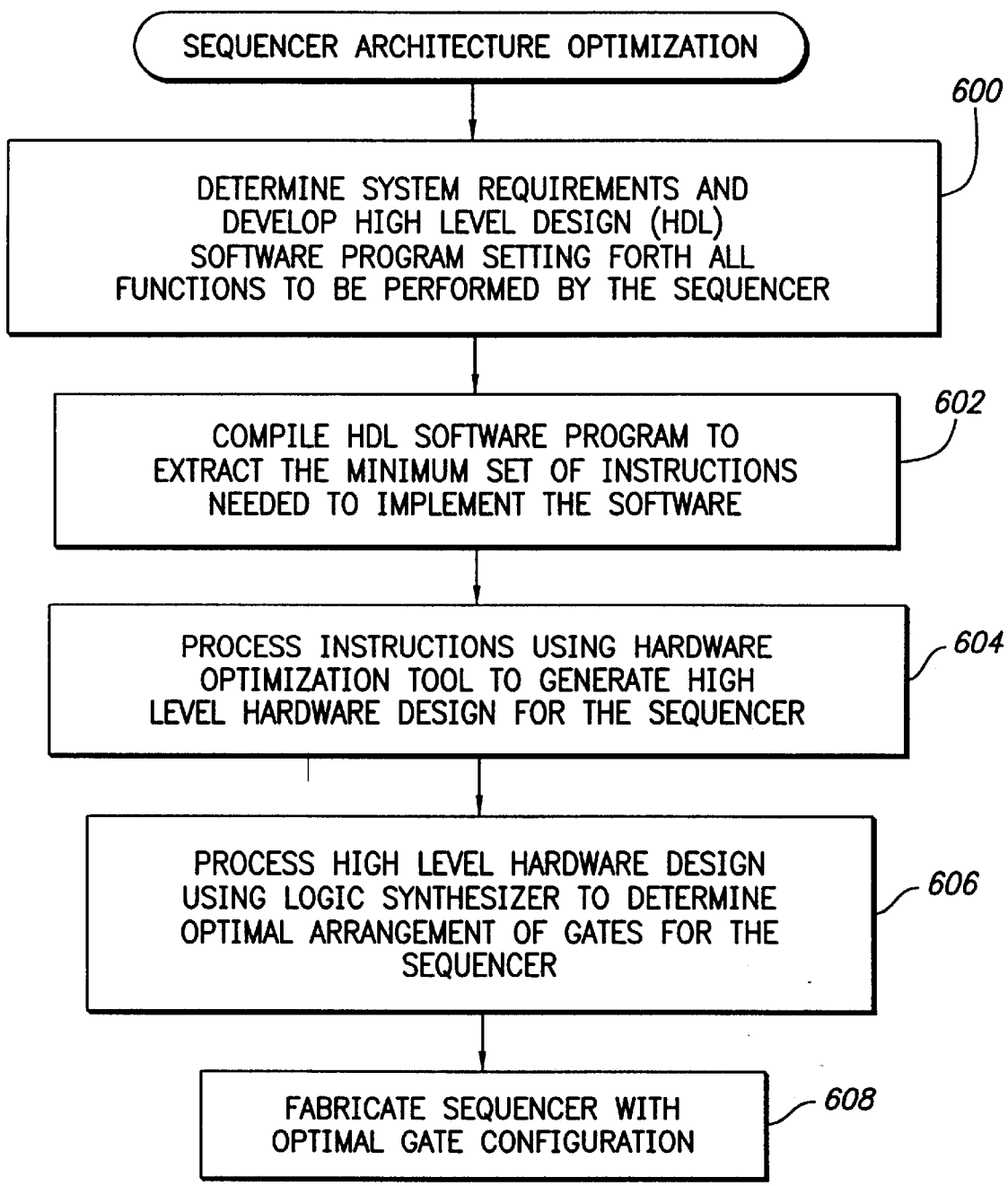
FIG. 19 is a flow chart illustrating a method for designing a hardware sequencer for use within the microcontroller of the implantable cardiac stimulation device of FIG. 1.

Thus, in contrast with many conventional hardware design techniques which merely optimize an IC gate configuration based upon a high-level hardware design, the method of FIG. 19 first optimizes the high-level hardware design based upon the software design, then optimizes the IC design based upon the optimized hardware design. Depending upon the particular implementation, the IC design may be optimized to, for example, minimize the number of transistor devices, the amount of circuit space, the amount of power consumption, the signal transmission routing delays, or some combination of these factors. For the specific example involving a sequencer for use in an implantable cardiac stimulation device, the specific functions to be performed by the sequencer are first determined at step 600 and represented via a high-level programming design language which sets forth the basic logic and operations to be performed by the sequencer. At step 602, the high-level design program is compiled to extract the set of instructions necessary to perform the functions, yielding a set of instructions such as represented in Table I above. The set of instructions are then processed at step 604 to determine the hardware devices required to perform each of the various instructions, i.e., to determine particular blocks of transistor gates for performing jump operations, resume operations, masking operations, and the like. The high-level hardware design is output in Verilog. At step 606, the Verilog output is then processed by the logic sequencer to generate the optimal arrangement of transistors for use in the IC so as to minimize power consumption, or any other selected factor. At step 606, the specific sequence of logic gates generated by the logic synthesizer are then employed in manufacturing an IC. As a result, the IC provides the optimal logic gate configuration for performing the specific functions of the sequencer as originally determined at step 600.

The method may also be applied to design an IC for the state crosspoint switch & control logic of the above-described state machine implementation. As can be appreciated, a wide variety of other hardware devices may be developed using the technique of FIG. 19 to achieve devices optimized to perform only specific functions. This technique is particularly useful for generating hardware devices for use in portable applications wherein power consumption is a critical factor and wherein the specific functions needed to be performed by the device can be determined in advance, as is often the case with implantable cardiac stimulation devices.

The various functional components of the exemplary system may be implemented using any appropriate technology including, for example, microprocessors running software programs or application specific integrated circuits (ASICs) executing hard-wired logic operations. Although described with respect to a pacemaker, aspects of the invention are applicable to other systems, such as systems employing other implantable cardiac stimulation devices. The exemplary embodiments of the invention described herein are merely illustrative of the invention and should not be construed as limiting the scope of the invention.

What is claimed is:

1. A method for designing a sequencer for use in an implantable cardiac stimulation device comprising the steps of:

developing a high-level software program setting forth the functions to be performed by the sequencer using a high-level software design language;

compiling the high-level software program to determine a minimum set of instructions needed to implement the functions;

processing the set of instructions using an automated hardware optimization tool to determine an optimal high-level hardware design for implementing the instructions;

processing the high-level hardware design using a logic synthesizer to determine an optimal gate configuration; and fabricating an integrated circuit sequencer incorporating the optimal gate configuration.

2. The method of claim 1 further including the steps of:

fabricating an implantable cardiac stimulation device having the integrated circuit sequencer and also having a sensing circuit for sensing a cardiac signal, an electrical therapy delivery circuit for delivering therapy to heart tissue, and a general purpose programmable microprocessor;

implanting the cardiac stimulation device into a patient;

sensing a cardiac signal of the patient using the sensing circuit of the cardiac stimulation device;

analyzing the cardiac signal using the programmable sequencer of the cardiac stimulation device to determine whether therapy is needed and controlling the electrical therapy delivery circuit of the cardiac stimulation device to deliver therapy using the programmable sequencer; and performing non-therapy-delivery operations of the cardiac stimulation device using the general purpose programmable microprocessor.

3. A system for designing a sequencer for use in an implantable cardiac stimulation device comprising:

an input device operative to input a high-level software program setting forth functions to be performed by the sequencer in a high-level software design language;

a compiler operative to compile the high-level software program to determine a minimum set of instructions needed to implement the functions;

an automated hardware optimization tool operative to processes the set of instructions to determine an optimal high-level hardware design for implementing the instructions; and a logic synthesizer operative to process the high-level hardware design to determine an optimal gate configuration.

4. A system of claim 3 further comprising a fabrication system operative to fabricate an integrated circuit sequencer incorporating the optimal gate configuration.

5. An implantable cardiac stimulation device having the integrated circuit sequencer of claim 4.

6. The implantable cardiac stimulation device of claim 5 also having
- a sensing circuit for sensing a cardiac signal from the heart tissue;
- an electrical therapy delivery circuit for delivering therapy to the heart tissue; and
- a general purpose programmable microprocessor; and
- wherein the programmable sequencer is operative to analyze the cardiac signal to determine whether therapy is needed and to control the electrical therapy delivery circuit to deliver therapy and wherein the general purpose programmable microprocessor is operative to perform non-therapy-delivering operations.

7. The implantable cardiac stimulation device of claim 6 wherein the microprocessor is a complex instruction set computing (CISC) processor or a reduced instruction set computing (RISC) processor.

8. The implantable cardiac stimulation device of claim 6 wherein the sequencer is an event-driven programmable state machine.

9. A system for designing a sequencer for use in an implantable cardiac stimulation device comprising:
- means for compiling a high-level software program setting forth functions to be performed by the sequencer to determine a minimum set of instructions needed to implement the functions;
- means for determining an optimal high-level hardware design for implementing the set of instructions; and
- logic synthesizer means for determining an optimal gate configuration from the high-level hardware design.

10. The system of claim 9 further comprising means for fabricating an integrated circuit sequencer incorporating the optimal gate configuration.

11. An implantable cardiac stimulation device having the integrated circuit sequencer of claim 10.

* * * * *